(12) United States Patent
Jadwizak et al.

(10) Patent No.: US 11,253,709 B2
(45) Date of Patent: Feb. 22, 2022

(54) ELECTRODE LEAD WITH CONTINUOUSLY VARIABLE FIXATION LENGTH

(71) Applicant: BIOTRONIK SE & Co. KG, Berlin (DE)

(72) Inventors: Detmar Jadwizak, Erkner (DE); Dajana Kaiser, Berlin (DE); Carsten Fruendt, Berlin (DE); Gordon Hillebrand, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 47 days.

(21) Appl. No.: 16/424,752

(22) Filed: May 29, 2019

(65) Prior Publication Data

US 2019/0374782 A1  Dec. 12, 2019

(30) Foreign Application Priority Data

Jun. 7, 2018 (DE) .................... 10 2018 113 594.7

(51) Int. Cl.
*A61N 1/05* (2006.01)
*A61N 1/375* (2006.01)
*A61B 90/00* (2016.01)

(52) U.S. Cl.
CPC .......... *A61N 1/37518* (2017.08); *A61B 90/39* (2016.02); *A61N 1/057* (2013.01); *A61N 1/0565* (2013.01); *A61N 1/37516* (2017.08); *A61B 2090/3966* (2016.02); *A61N 2001/0578* (2013.01); *A61N 2001/0585* (2013.01)

(58) Field of Classification Search
CPC ............ A61N 1/37518; A61N 1/37516; A61N 1/0565; A61N 1/057; A61N 2001/0578; A61N 2001/0585; A61B 90/39; A61B 2090/3966
See application file for complete search history.

(56) References Cited

U.S. PATENT DOCUMENTS

| | | | |
|---|---|---|---|
| 5,170,802 A | 12/1992 | Mehra | |
| 5,387,233 A | 2/1995 | Alferness et al. | |
| 5,411,546 A | 5/1995 | Bowald et al. | |
| 5,476,498 A | 12/1995 | Ayers | |
| 2004/0059404 A1 | 3/2004 | Bjorklund et al. | |
| 2005/0043765 A1* | 2/2005 | Williams | A61N 1/057 607/9 |
| 2005/0137671 A1* | 6/2005 | Liu | A61N 1/0568 607/122 |

(Continued)

FOREIGN PATENT DOCUMENTS

| | | |
|---|---|---|
| DE | 10153842 A1 | 5/2003 |
| EP | 0546414 A1 | 6/1993 |

(Continued)

OTHER PUBLICATIONS

German Search Report for German Case No. DE 10 2018 113 594.7, dated Aug. 22, 2018 (8 pages).

*Primary Examiner* — Ankit D Tejani
*Assistant Examiner* — Joshua Brendon Solomon
(74) *Attorney, Agent, or Firm* — Buchanan Ingersoll & Rooney PC

(57) ABSTRACT

An electrode lead for the coronary sinus, with a lead body that has a distal section for insertion into the coronary sinus, and at least one electrode to make contact with body tissue, the at least one electrode being arranged on the distal section of the lead body. The electrode lead has a fixation device that can be extended out of the lead body to fix the electrode lead in a blood vessel.

14 Claims, 7 Drawing Sheets

(56) References Cited

U.S. PATENT DOCUMENTS

| | | |
|---|---|---|
| 2006/0036307 A1 | 2/2006 | Zarembo et al. |
| 2007/0239247 A1 | 10/2007 | Camps et al. |
| 2008/0077220 A1* | 3/2008 | Reddy .................... A61N 1/057 |
| | | 607/131 |
| 2009/0248117 A1* | 10/2009 | Nippoldt ................ A61N 1/056 |
| | | 607/60 |
| 2010/0256719 A1 | 10/2010 | Bjorklund et al. |
| 2011/0022057 A1* | 1/2011 | Eigler .................... A61M 25/09 |
| | | 606/129 |
| 2011/0106099 A1 | 5/2011 | Duffy et al. |
| 2014/0155966 A1* | 6/2014 | Sethna .................... A61N 1/05 |
| | | 607/116 |
| 2015/0112415 A1 | 4/2015 | Weitzig et al. |
| 2015/0306380 A1 | 10/2015 | Sommer et al. |
| 2016/0059006 A1* | 3/2016 | Doan .................. A61N 1/0573 |
| | | 607/127 |
| 2017/0165475 A1* | 6/2017 | Kaiser ................ A61B 17/3468 |

FOREIGN PATENT DOCUMENTS

| | | |
|---|---|---|
| WO | 9407564 A2 | 4/1994 |
| WO | 98042403 A1 | 10/1998 |

* cited by examiner

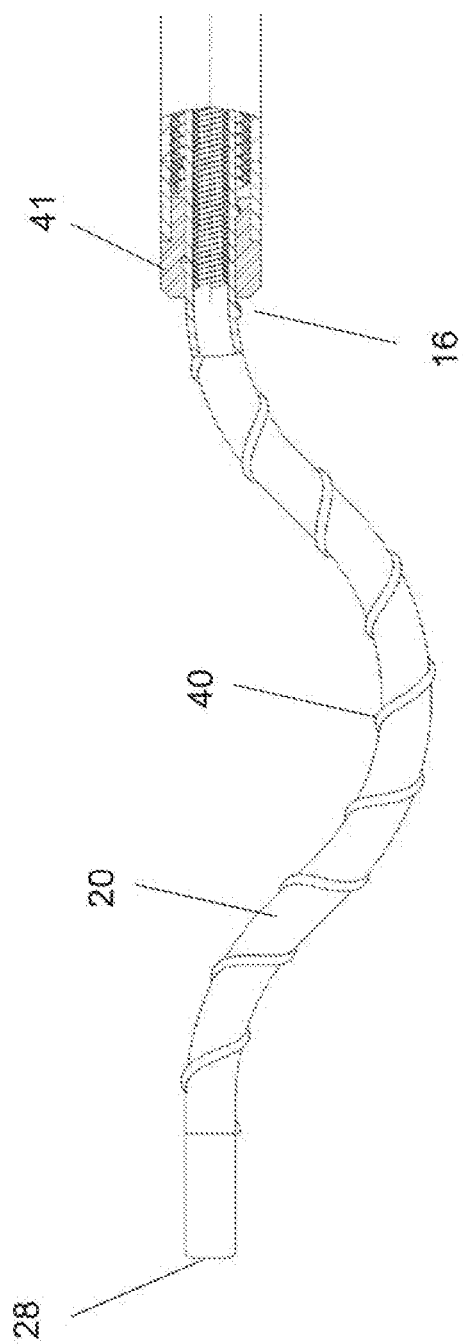

ELECTRODE LEAD WITH CONTINUOUSLY VARIABLE FIXATION LENGTH

CROSS-REFERENCE TO RELATED APPLICATIONS

This patent application claims the benefit of and priority to co-pending German Patent Application No. DE 10 2018 113 594.7, filed on Jun. 7, 2018 in the German Patent Office, which is hereby incorporated by reference in its entirety.

TECHNICAL FIELD

The present invention relates to an electrode lead that is connectable with a pulse generator and that has electrodes to make contact with body tissue for cardiac resynchronization therapy ("CRT").

BACKGROUND

An especially simple fixation technique to avoid dislocations of such electrode leads in the coronary sinus area is to wedge the distal end of the lead body in a vessel. This involves pushing the electrode lead forward, for example in the vein branches of the coronary sinus, until the distal end of the lead body gets stuck in the tapering vein and assumes a "wedge position". In this position, the vein is occluded by the electrode lead.

However, the possibility of secure fixation of the electrode lead by means of such a wedge position is strongly dependent on the geometry (e.g., the course, length, and diameter, etc.) of the target vein in the coronary sinus. Therefore, the final position of the stimulation and/or sensing electrode(s) is determined for the most part by the geometry of the target vein, and does not necessarily correspond to the best place for the therapy.

For the printed prior art, please refer, for example, to International Publication No. WO 98/42403 or U.S. Pat. No. 5,170,802. These publications disclose a fixation device with a so-called "stent", which is expanded if the electrode lead is located at the desired position in the vessel. Expansion of the stem structure clamps the lead body in the position. The disadvantage of this solution is that the fixation is not reversible, which makes it difficult to detach the electrode lead and move it to a different place after a first fixation, which is sometimes necessary, and also makes it difficult to remove the electrode lead.

International Publication No. WO 94/07564 discloses a solution to the problem of moving the electrode lead to a different place, which involves fixing the electrode lead by an expandable or self-expanding wire basket. The disadvantage of this design is that the wires cut into the vascular wall, and thus can be very traumatic.

Finally, U.S. Pat. No. 5,411,546 shows various solutions for fixation in a vessel, for example wire helices that are reversibly extendable out of the catheter sheath and that can be withdrawn back into it. However, the small diameter of the wires and the resulting small contact surface between helices and vascular wall, and the only limited tension force with which the helices may press against the vascular wall in order not to damage the latter makes the fixation not very reliable. The wire constructions further disclosed in the publication are—as was already mentioned above—highly traumatic. This published prior art also shows a so-called "sail design", which once again is not reversible.

Please also refer to U.S. Publication No. 2006/0036307. These disclose implantable cardiovascular pacemaker or defibrillator electrode devices, which comprise a long, stretched-out tubular electrode body and a fixation zone in the distal end area of the electrode body. The fixation zone has an outwardly closed peripheral sleeve and serves for detachable fixation of the electrode device in a body lumen, by being reversibly expandable. The expansion and contraction are controlled by expansion means arranged in the fixation zone.

In addition to these features, European Patent No. 0 546 414 shows an electrode device in which the expansion means are formed by pneumatic or hydraulic pressurization, with the help of which the flexible wall of the electrode body in the fixation zone is reversibly expandable. However, it is difficult to produce a wall that is permanently sealed, so that it has been found that over time the mentioned solutions lose their expanded form, and thus the fixation. Furthermore, the expansion force of the flexible wall is limited.

The present invention is directed at overcoming one or more of the above-mentioned problems. Starting from this prior art, the present invention has a goal of creating an electrode lead that is improved with respect to the problems mentioned above.

SUMMARY

At least this problem is solved by an electrode lead having the features of claim 1. Advantageous embodiments of the present invention are indicated in the corresponding subordinate claims and are described below.

Claim 1 discloses an electrode lead for the coronary sinus with:

a lead body that is preferably long and stretched-out, in particular one that extends along a longitudinal axis, the lead body having a distal section for insertion into the coronary sinus, and at least one electrode to make contact with body tissue, the at least one electrode being arranged on the distal section of the lead body.

The present invention now provides that the electrode lead has a fixation device to fix the electrode lead in a blood vessel, this fixation device being extendable out of the lead body, in particular extendable in the direction of the longitudinal axis.

This fixation device is preferably variably extendable out of the lead body, so that a section that is extended out of the lead body has an adjustable length (in particular, in the direction of the longitudinal axis).

In the context of this invention, the proximal end or the proximal section of the lead body is, in particular, that end or that area through which the lead body will be or has been connected with a pulse generator. Accordingly, the distal end or the distal section of the lead body is, in particular, that end or that section of the lead body that is farther away from the pulse generator.

The electrode lead can optionally comprise two or more electrodes to make contact with body tissue, the at least two electrodes being arranged on the distal section of the lead body, in particular being arranged spaced apart from one another along the longitudinal axis. A second electrode also allows a bipolar stimulation of the tissue, along with the unipolar stimulation.

Given the (optimal) position of the at least one electrode, the inventive solution advantageously simultaneously allows, by the distally extendable fixation device, secure fixation of the electrode conductor in a target vein of the coronary sinus.

This makes it possible to select, in each case, an optimal electrode position and simultaneously an optimal fixation position of the electrode conductor or the fixation device.

This also means that the present invention makes it possible to eliminate the otherwise necessary selection of the fixation variant and, in the case of bipolar stimulation, the separations of the electrodes from one another. In particular, the variability of the fixation device makes it possible to eliminate the frequent use of leads with 4 electrodes, which offers a larger selection of electrode positions when non-variable fixation is used, however is less economical due to the larger number of electrodes.

Furthermore, the present invention advantageously offers the possibility of using the same electrode conductor if it is necessary to select another target vein during implantation (e.g., a longer vein).

One embodiment of the present invention provides that the fixation device be movably arranged in a receptacle formed by the lead body, allowing the fixation device to be extended out of the lead body (in particular in the direction of the longitudinal axis of the lead body) through an opening of the receptacle, this opening being arranged on a distal end of the lead body.

One embodiment of the present invention further provides that the respective electrode be connected with an electrical conductor that is arranged in an interior of the lead body. The electrical conductors can be in the form of a cable, for example, if there are multiple electrical conductors, it is possible to use multiple cables which are routed essentially parallel to one another, for example. A separate channel can be provided for each electrical conductor in the form of a cable, or a common channel can be provided for multiple or all electrical conductors in the form of cables. If multiple electrical conductors in the form of a cable are routed in a common channel, it is expedient if the individual conductors are insulated from one another.

One embodiment of the present invention further provides that the respective electrical conductor extend helically around the said receptacle, i.e., the respective conductor helically surrounds the fixation device if the latter is in a retracted state or at least sections of it are arranged in the said receptacle.

One embodiment of the present invention further provides that if there are two or more electrical conductors, these electrical conductors are arranged coradial to one another. In particular, this involves the individual electrical conductors being insulated from one another and wound into a multiply wound helix, in which the two electrical conductors form congruent helices that have the same diameter and pitch and that intertwine with one another.

One embodiment of the present invention further provides that the lead body have a proximal end, in particular one that lies opposite the distal section in the direction of the longitudinal axis of the lead body, and that there be arranged at this proximal end of the lead body a connection device to connect the electrode lead to an implantable pulse generator, the respective electrical conductor being connected with an associated contact of the connection device. The connection device can be a plug. It is preferable to use IS-1 plugs or IS4 plugs.

One embodiment of the present invention further provides that a section of fixation device extended out of the lead body be designed to be deformed into a defined shape, in particular, this section being designed to be deformed out of a linear or stretched-out shape into a shape deviating from the linear shape, the defined shape of the section causing, in particular, the fixation device and, along with it, the electrode lead to be fixed in the blood vessel.

One embodiment of the present invention further provides that the defined shape correspond to one of the following shapes: a helix, an S-curve, a meandering structure, or a J-curve.

One embodiment of the present invention further provides that the fixation device have a preformed helix to deform the said section. The helix can be a helical element made of a metal, the metal preferably being MP35N, stainless steel, tantalum, platinum, palladium, or silver (individually or in combination, e.g. MP35N with a silver core).

One embodiment of the present invention further provides that the said helix be soft-annealed in a proximal area, so that it can be drawn for arrangement in the receptacle of the lead body. Furthermore, a distal area of the helix can be annealed into a plastically less easily deformable area, which forms the said defined shape.

One embodiment of the present invention provides that the helix extend along the longitudinal axis over an entire length of the fixation device or only over a distal area of the fixation device.

One embodiment of the present invention provides that the helix of the fixation device have, on an inner surface of the helix, insulation, in particular in the form of a polymer tube, and/or that the helix of the fixation device have, on an outer surface of the helix, insulation, in particular in the form of a polymer tube.

One embodiment of the inventive electrode lead further provides that the fixation device be extendable by means of a screwing motion.

One embodiment of the present invention further provides that the fixation device have an external thread that engages with an internal thread of the lead body, allowing the fixation device to be screwed out of the lead body and thereby extended.

One embodiment of the present invention further provides that the electrode lead have a rotatable plug, so that rotating the plug allows the fixation device to be screwed out of the lead body and thereby extended. The plug is preferably an IS-1 plug or IS4 plug that has a rotatable plug pin (pin), so that rotation on the pin allows the fixation device to be screwed out of the lead body and thereby extended.

One embodiment of the present invention further provides that the fixation device have a lumen for insertion of a mandrel into the fixation device, the fixation device being designed to be extended or screwed out of the lead body by means of a mandrel inserted into the lumen, in particular the helix of the fixation device extending around the lumen of the fixation device. In particular, the lumen is aligned with a passage on the connection device (e.g., a drill hole on the pin of the IS-1 or IS4 plug), so that the mandrel can be inserted into the lumen through the passage from the proximal end of the lead body.

One embodiment of the present invention further provides that the fixation device have a sleeve on a distal end of the fixation device that forms a stop for a mandrel, so that the fixation device can be extended out of the lead body by the mandrel being inserted into the lumen of the fixation device and this mandrel being pressed against the stop, or the fixation device being able to engage with the mandrel in such a way that the mandrel can screw the fixation device out of the lead body and thereby extend it.

In both cases, the sleeve can further be configured to engage with a mandrel so that the fixation device can be retracted again by means of the mandrel, e.g., by pulling on the mandrel, so that the fixation device is retracted back into the lead body or by screwing the fixation device into the lead body so that the fixation device is retracted back into the lead body.

One embodiment of the present invention further provides that the fixation device be designed to be locked in place with respect to the blood vessel and the lead body if a mandrel arranged in the lumen is pulled out of the lumen.

One embodiment of the present invention further provides that the lead body have, at the distal end of the lead body, a clamping device to lock the fixation device in place (and to seal the lead body), the clamping device being able to form the said opening, and the clamping device being designed to clamp the fixation device, if a mandrel arranged in the lumen is pulled out of the lumen.

In particular, the clamping device can be a clamping sleeve provided at the distal end of the lead body, this clamping sleeve having or forming, in particular, the said opening to extend the fixation device.

One embodiment of the present invention further provides that the fixation device have at least one X-ray marker to measure a length of the extended section of the fixation device, this X-ray marker being fixed on the fixation device, in particular on the helix of the fixation device, and at least one X-ray marker that is fixed on the lead body, in particular on one of the coradial electrical conductors.

Additional features, aspects, objects, advantages, and possible applications of the present invention will become apparent from a study of the exemplary embodiments and examples described below, in combination with the Figures, and the appended claims.

DESCRIPTION OF THE DRAWINGS

The discussion below is intended to describe other features, advantages, and embodiments of this invention on the basis of the Figures. The Figures are as follows:

FIG. 7 shows a distal end of one embodiment of an inventive electrode lead in the extended state, with thread.

DETAILED DESCRIPTION

Figure 1:
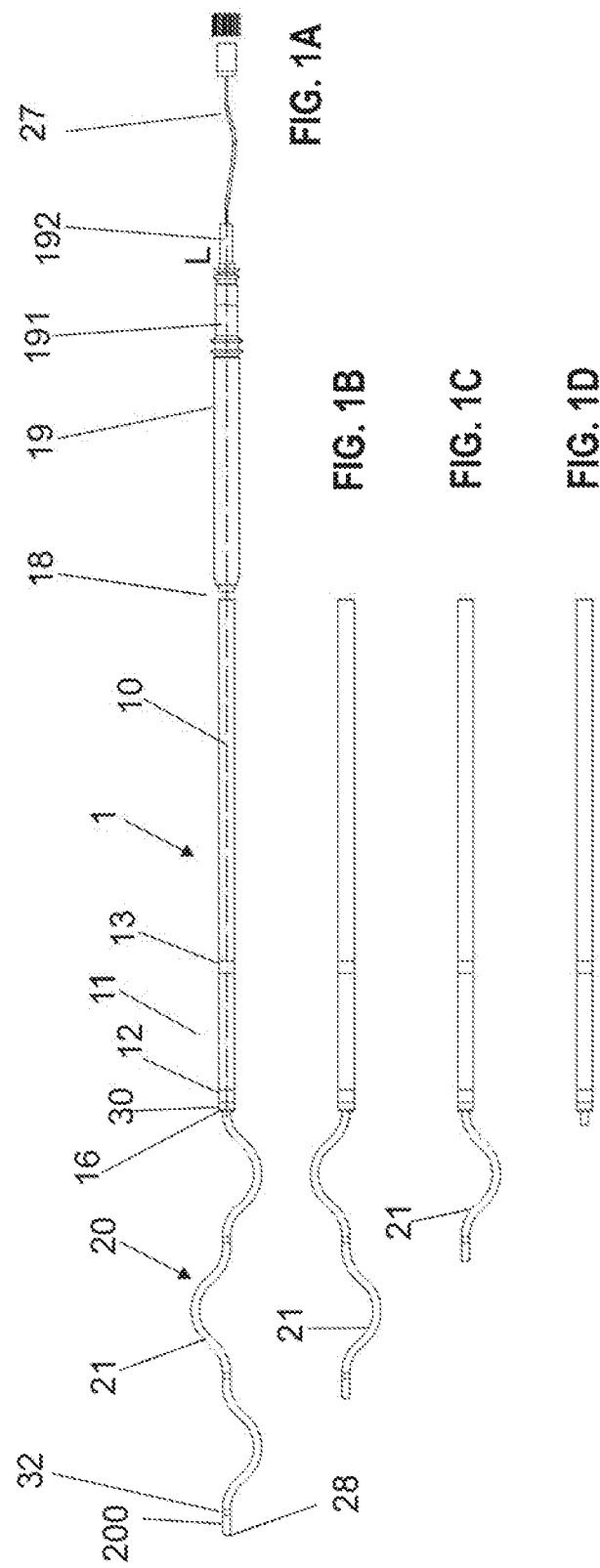
FIGS. 1A-1D show an embodiment of an inventive electrode lead with fixation devices that have been extended different distances in the distal section, FIGS. 1A through 1D.

An embodiment of the present invention is described below using inventive electrode leads 1, which are suitable for use in the coronary sinus and which comprise two electrodes 12, 13 to make contact with body tissue. Such electrode leads 1 are also referred to as bipolar electrode leads. However, the present invention is also feasible with electrode leads with only one electrode (unipolar electrode leads) or with more than two electrodes (multipolar electrode leads).

FIGS. 1A-11D, in connection with FIGS. 2 through 7, shows an embodiment of an inventive electrode lead 1 for use in the coronary sinus. The electrode lead 1 has a preferably long, stretched out lead body 10, that extends along a longitudinal axis L and that has a distal section 11 for insertion into the coronary sinus. Furthermore, the electrode lead has two or even more (e.g., 3 or 4) electrodes 12, 13 to make contact with body tissue, each of which can be configured as a stimulation electrode or as a sensing electrode. The at least two electrodes 12, 13 are, in particular, ring-shaped and are arranged spaced apart from one another in the direction of the longitudinal axis L of the lead body 10 on the distal section 11 of the lead body 10.

The present invention now provides that the electrode lead 1 have a fixation device 20 to fix the electrode lead 1 in a blood vessel, in this case in a target vein of the coronary sinus, this fixation device 20 being extendable out of the lead body 10, in particular extendable in the direction of the longitudinal axis L. This fixation device 20 is variably extendable out of the lead body 10, so that when the fixation device 20 is extended out of the lead body 10, the section 21 that is extended has an adjustable length in the direction of the longitudinal axis L, as is shown in FIGS. 1A through 1D.

FIG. 1A shows a fixation device 20 that has been completely extended out of the lead body 10, a section 21 of the extended fixation device 20 assuming, after being extended, a defined shape, which fixes it in the blood vessel. FIGS. 1B and 1C show fixation devices 20 that are extended less far out. Finally, FIG. 1D shows an essentially retracted fixation device 20, which can represent a normal state of the electrode lead 1; starting from this normal state, the section 21 to be extended can be brought to a necessary length (in the direction of the longitudinal axis L), which on the one hand securely anchors the electrode lead in the selected blood vessel of the coronary sinus and, on the other hand, allows correct positioning of the electrodes 12, 13 once the electrode lead 1 has been fixed.

Figure 2:
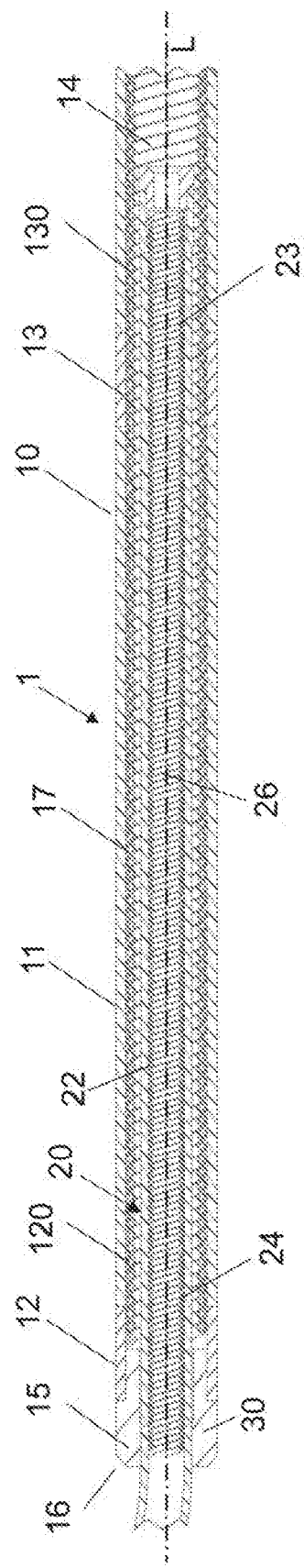
FIG. 2 shows a sectional view of a distal section of an embodiment of an inventive electrode lead with a partly retracted fixation device.
Figure 3:
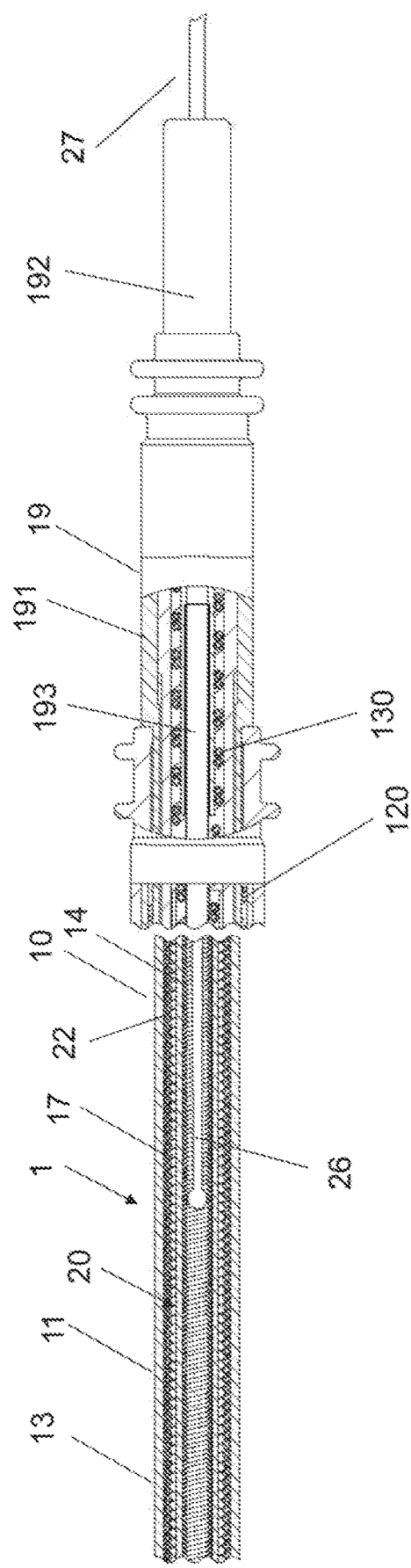
FIG. 3 shows an enlarged detail of FIG. 2.
Figure 4:
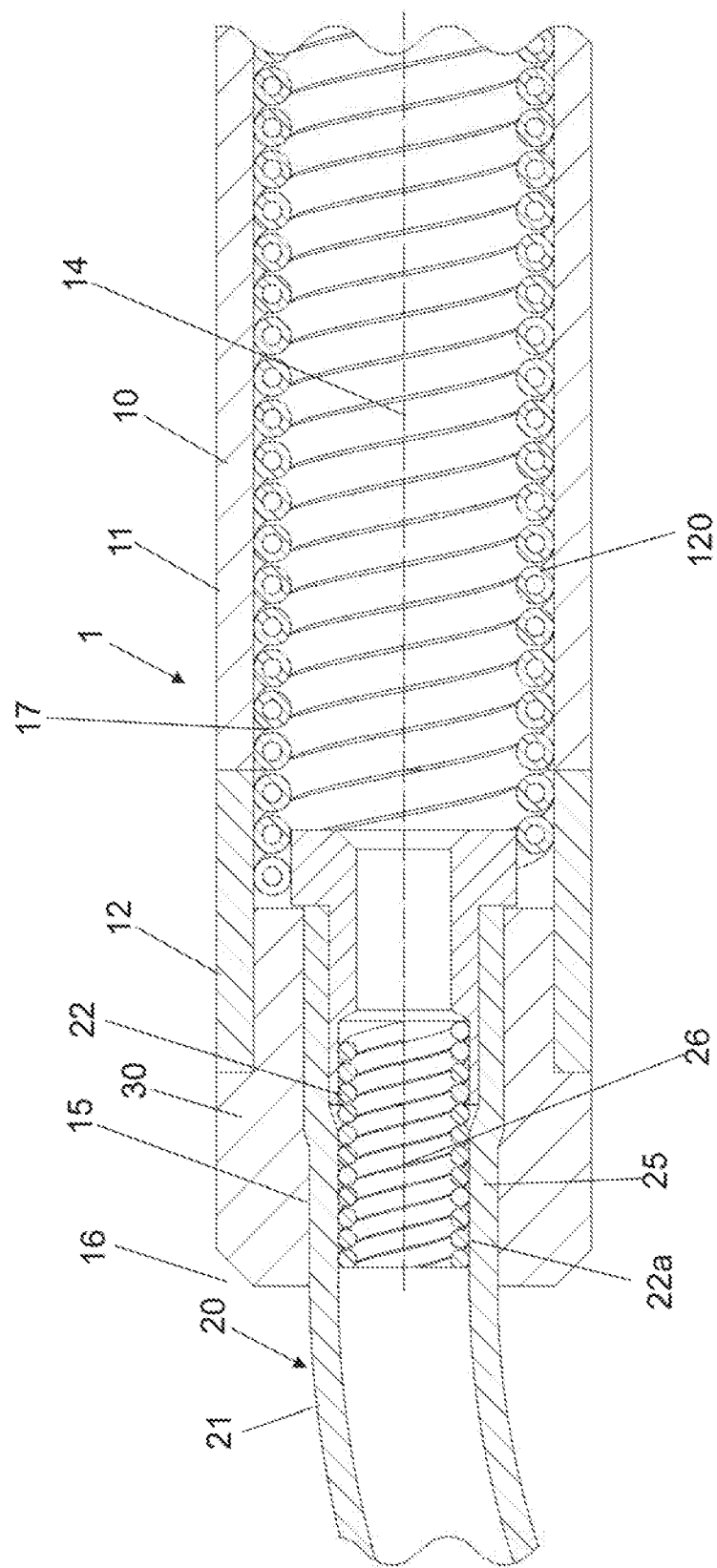
FIG. 4 shows a distal end of the electrode lead shown in FIGS. 1 through 3, in extended state.
Figure 6:
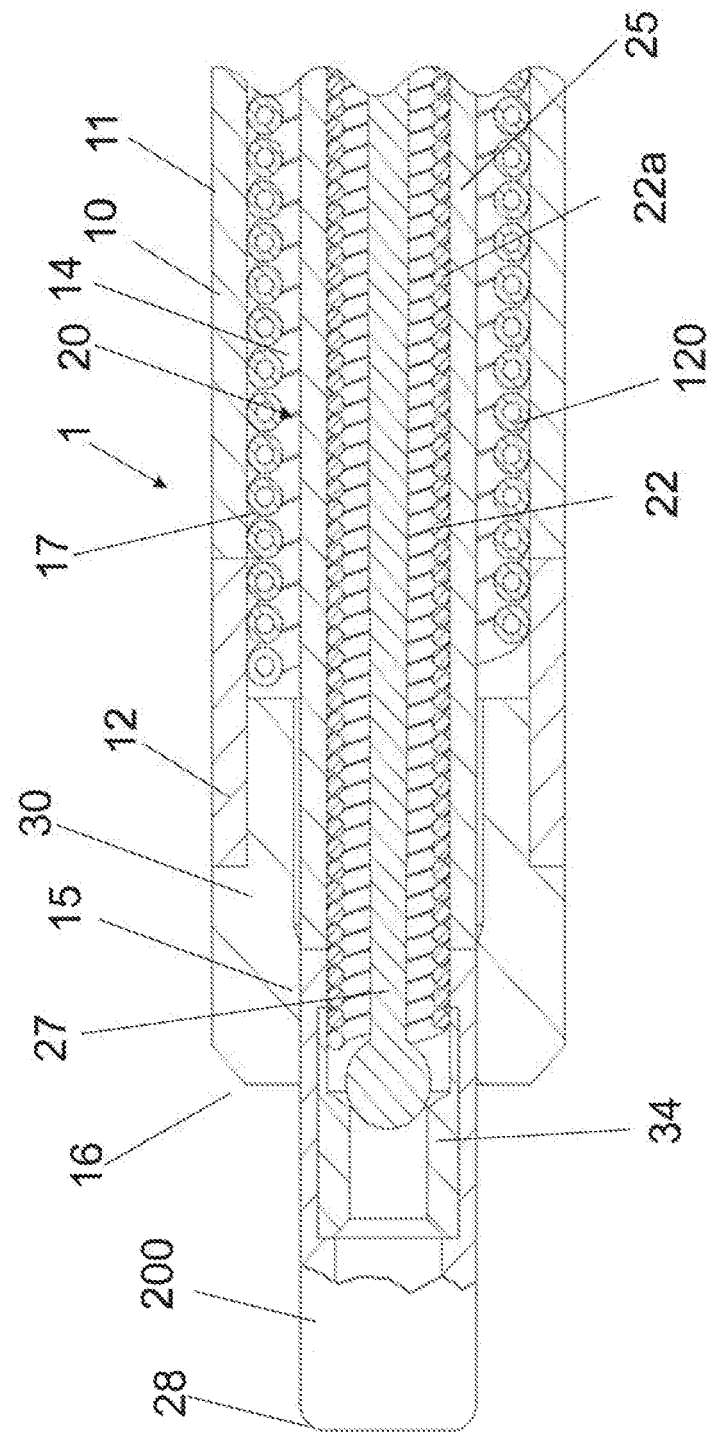
FIG. 6 shows the distal end according to FIG. 5 in a retracted fixation device.

As is shown especially in FIGS. 2 through 4 and 6, the fixation device 20 is preferably movably arranged in a receptacle 14 provided in the lead body 10, so that the fixation device 20 can be extended out of the lead body 10 in the direction of the longitudinal axis L through an opening 15 in the lead body 10, the opening 15 being arranged on a distal end 16 of the lead body 10 (see especially FIGS. 4 and 6).

As is also indicated, e.g., in FIG. 2, it is preferably provided that the respective electrode 12, 13 be connected with an electrical conductor 120, 130 that is arranged in an interior 17 of the lead body 10, the respective electrical conductor 120, 130 extending helically around the said receptacle 14 for the fixation device 20 or around the fixation device 20 itself, if the latter is in an retracted state or if at least sections of it are arranged in the said receptacle 14 (see especially FIGS. 2, 3 and 6). The conductors 120, 130 are preferably in the form of coradial helices, i.e., the individual electrical conductors 120, 130 are insulated from one another and wound into a multiply wound helix.

According to FIG. 1A, the lead body 10 also has a proximal end 18, in particular a proximal end 18 that lies opposite the distal section 11 of the lead body in the direction of the longitudinal axis L, the proximal end 18 having a connection device 19 arranged on it to connect the electrode lead 1 to an implantable pulse generator, and the respective electrical conductor 120, 130 being connected with an associated contact 192, 191 of the connection device 19, so that the electrodes 12, 13 are connectable in an electrically conductive manner with the pulse generator. If the electrode lead is optionally equipped with more than two electrodes, the connection device 19 can also be equipped with more than two contacts. The contact 191 can be in the form of an annular contact and the contact 192 can be in the form of a plug pin (pin).

To deform the respectively extended section 21 of the fixation device 20, the electrode lead has, in particular, a preformed helix 22, as is shown in FIGS. 2 through 7. This can involve a proximal area 23 (see FIG. 2) of the helix 22 being soft-annealed, so that it can be drawn (e.g., by means of a mandrel 27) for arrangement in the receptacle 14 of the lead body 10, while a distal area 24 of the helix 22 (see FIG. 2) can be annealed into a plastically less easily deformable area, which can form the said defined shape that anchors the fixation device 20 (see also FIGS. 1A through 1D).

Figure 5:
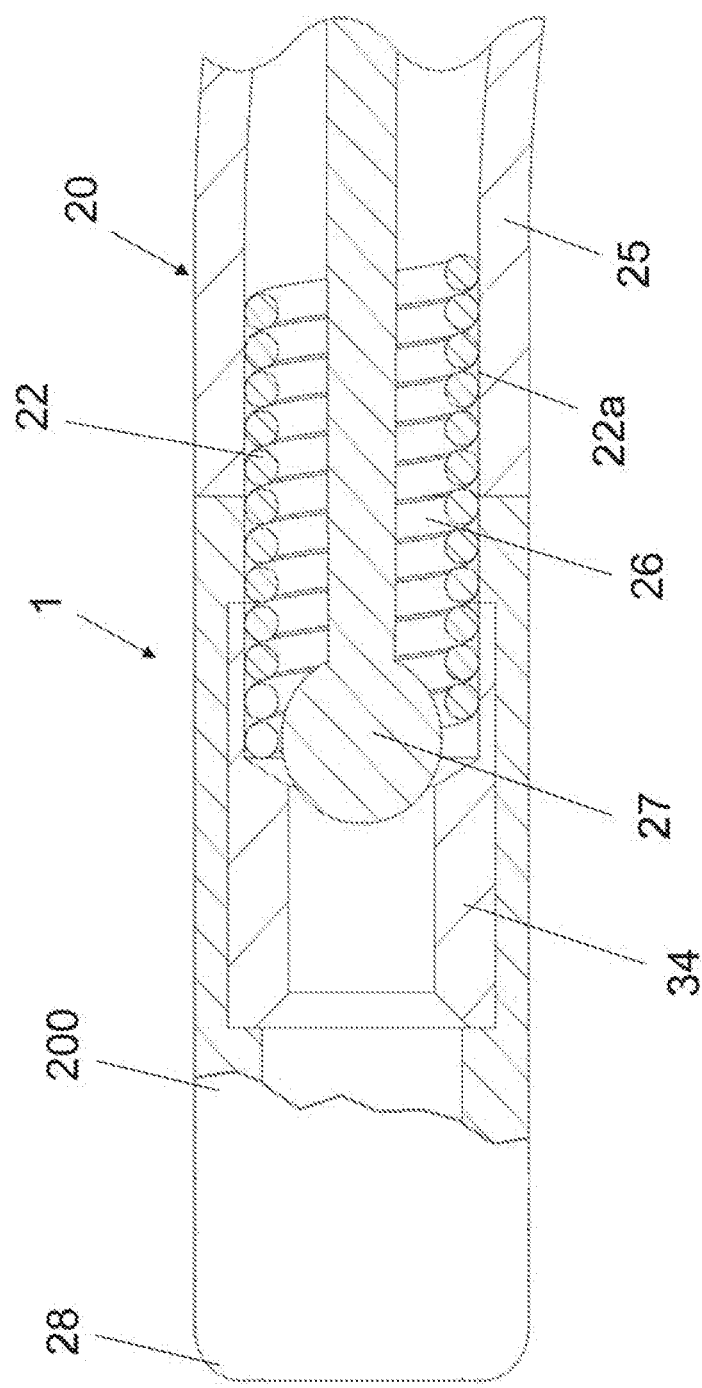
FIG. 5 shows a distal end of the fixation device of the electrode lead shown in FIGS. 1 through 4, with a stop for a mandrel.

The fixation device 20 can also have, on an outer surface 22a of the helix 22, an insulation e.g., in the form of a polymer tube that surrounds the helix 22, as is shown, e.g., in FIGS. 4 through 6.

One embodiment can provide that the helix 22 of the fixation device 20 have, on an inner surface of the helix, an insulation, in particular in the form of a polymer tube, and/or that the helix of the fixation device have, on an outer surface 22a of the helix 22, an insulation 25, in particular in the form of a polymer tube.

To extend the fixation device 20 out of the lead body 10, to produce, e.g., the configurations shown in FIG. 1A through FIG. 1C, it can be provided that the fixation device 20 have a lumen 26 for insertion of a mandrel 27 into the fixation device 20, the fixation device 20 preferably being designed to be extended out of the lead body 10 by means of a mandrel 27 inserted into the lumen 26, the helix 22 of the fixation device 20 extending, in particular, around the lumen 26 of the fixation device 20. In particular, the lumen 26 is aligned with a passage 193 on the connection device 19, so that the mandrel 27 can be inserted into the lumen 26 from the proximal end 18 of the lead body 10 through the passage 193.

Furthermore, the fixation device 20 has, on a distal end 28 of the fixation device 20, a sleeve 200, preferably according to FIG. 5, that forms a stop 34 for a mandrel 27, so that the fixation device 20 can be extended out of the lead body 10 by means of the mandrel 27, which is inserted into the lumen 26 of the fixation device 20 and is pressed against the stop 34, or by means of the fixation device, which is able to engage with the mandrel 27 in such a way that the mandrel 27 can screw the fixation device 20 out of the lead body and thereby extend it. In another embodiment, the fixation device 20 can have, for this purpose, an external thread 40 that engages with an internal thread 41 of the lead body 10, as is shown in FIG. 7. In both cases, the sleeve 200 can further be configured to engage with a mandrel 27 so that the fixation device 20 can also be retracted again by means of the mandrel 27, by pulling on the mandrel, so that the fixation device 20 is retracted back into the lead body 10, or by screwing the fixation device 20 into the lead body 10 so that the fixation device 20 is retracted back into the lead body 10.

The sleeve 200 and the stop 34 can further have a passage, so that the electrode lead 1 can be inserted over a guide wire (not shown) (OTW=over the wire). Furthermore, there can be, in the sleeve 200 or proximal to the stop 34, a gasket or a lock system that seals the lumen 26 of the electrode lead 1 at the distal end 28 of the fixation device 20. The lock system or the gasket prevents the penetration of body fluid into the lumen 26 of the electrode lead 1.

Furthermore, the fixation device 20 is preferably designed to be locked in place with respect to the lead body 10 (e.g., in an extended state of the type shown in FIGS. 1A through 1C), if a mandrel 27 arranged in the lumen 26 is pulled out of the lumen 26.

In particular, to lock, the fixation device 20 in place, the lead body 10 can have, at the distal end 16 of the lead body 10, a clamping device 30 that is preferably in the form of a clamping sleeve 30 and that defines the said opening 15 through which the fixation device 20 can be extended out of the lead body 10. The clamping sleeve 30 is preferably designed to clamp the fixation device 20 if a mandrel 27 arranged in the lumen 26 of the fixation device 20 is pulled out of the lumen 26 (at the proximal end of the lead body).

According to another embodiment of the present invention, the electrode lead 1 can have, to measure the length of the extended section 21 of the fixation device 20, one X-ray marker on the lead body 10 and at least one other X-ray marker 32 on the fixation device 20. The function of the X-ray marker on the lead body 10 can be performed, e.g., by the clamping sleeve 30, if the latter is made of a radiopaque material. The distance between the clamping sleeve 30, which is functioning as an X-ray marker, and the X-ray marker 32 is visible in the X-ray picture and makes it possible to estimate how far the fixation device 20 is extended.

Current CRT electrodes do not always allow optimal CRT therapy under all anatomical relationships. The continuously variable length of the fixation device offered by the inventive solution provides an optimal implantation site and simultaneously secure fixation of the electrode lead 1 under all anatomical vein constellations. In particular, this allows the use of economical one-electrode or two-electrode electrode leads. Furthermore, the doctor can, in particular during the implantation, adjust the fixation length as needed.

It will be apparent to those skilled in the art that numerous modifications and variations of the described examples and embodiments are possible in light of the above teachings of the disclosure. The disclosed examples and embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. An electrode lead for the coronary sinus, comprising:
   a lead body that has a distal section for insertion into the coronary sinus; and
   at least one electrode to make contact with body tissue, the at least one electrode being arranged on the distal section of the lead body,
   wherein the electrode lead has a fixation device that can be extended out of the lead body to fix the electrode lead in a blood vessel,
   wherein the fixation device has a linear shape inside of the lead body,
   wherein a section of the fixation device extended out of the lead body is designed to be deformed into a defined shape deviating from the linear shape,
   wherein the fixation device is movably arranged in a receptacle arranged in the lead body, so that the fixation device can be extended out of the lead bod through an opening in the lead body, the opening being arranged on a distal end of the lead body, and
   wherein the lead body has, on the distal end of the lead body, a clamping sleeve to lock the fixation device in place, the clamping sleeve forming the opening through which the fixation device is extended, and the clamping sleeve being designed to clamp around the fixation device, if a mandrel arranged in the lumen is pulled out of the lumen at a proximal end of the lead body.

2. The electrode lead according to claim 1, wherein the electrode is connected with an electrical conductor that is arranged in an interior of the lead body, the electrical conductor extending helically around the said receptacle.

3. The electrode lead according to claim 2, wherein the electrode lead comprises at least two electrodes to make contact with body tissue, the at least two electrodes being arranged on the distal section of the lead body, the respective electrode being connected with an electrical conductor that is arranged in an interior of the lead body, the respective electrical conductor extending helically around the said receptacle and the electrical conductors being arranged coradial to one another.

4. The electrode lead according to claim 2, wherein the lead body has a proximal end, the proximal end having a connection device arranged on it to connect the electrode lead to an implantable pulse generator, and the respective electrical conductor being connected with an associated contact of the connection device.

5. The electrode lead according to claim 1, wherein the defined shape corresponds to one of the following shapes: a helix, an S-curve, a meandering structure, or a J-curve.

6. The electrode lead according to claim 1, wherein the fixation device has a preformed helix to deform the said section.

7. The electrode lead according to claim 1, wherein the fixation device has an external thread that engages with an internal thread of the lead body, allowing the fixation device to be screwed out of the lead body and thereby extended.

8. The electrode lead according to claim 1, wherein the electrode lead has a rotatable plug, so that rotating the plug allows the fixation device to be screwed out of the lead body and thereby extended.

9. The electrode lead according to claim 1, wherein the fixation device has a lumen for insertion of the mandrel into the fixation device, the fixation device being designed to be extended out of the lead body by means of the mandrel inserted into the lumen.

10. The electrode lead according to claim 1, wherein the fixation device has a sleeve on a distal end of the fixation device, that forms a stop for the mandrel.

11. The electrode lead according to claim 1, wherein the fixation device is designed to be locked in place with respect to the lead body, if the mandrel arranged in the lumen is pulled out of the lumen.

12. An electrode lead for the coronary sinus, comprising:

a lead body that has a distal section for insertion into the coronary sinus; and at least one electrode to make contact with body tissue, the at least one electrode being arranged on the distal section of the lead body, wherein the electrode lead has a fixation device that can be extended out of the lead body to fix the electrode lead in a blood vessel, wherein the fixation device is movably arranged in a receptacle arranged in the lead body, so that the fixation device can be extended out of the lead body through an opening in the lead body, the opening being arranged on a distal end of the lead body, and wherein the lead body has, on the distal end of the lead body, a clamping sleeve to lock the fixation device in place, the clamping sleeve forming the opening through which the fixation device is extended, and the clamping sleeve being designed to clamp around the fixation device, if a mandrel arranged in the lumen is pulled out of the lumen at a proximal end of the lead body.

13. The electrode lead according to claim 1, wherein the fixation device has at least one X-ray marker to measure a length of the extended section of the fixation device, this X-ray marker being fixed on the fixation device, and at least one X-ray marker that is fixed on the lead body.

14. The electrode lead according to claim 1, wherein a proximal area of the fixation device is soft annealed, and wherein a distal area of the fixation device is annealed to be less easily deformable than the proximal area of the fixation device.

* * * * *